United States Patent [19]

Sudrabin et al.

[11] 4,235,688
[45] Nov. 25, 1980

[54] SALT BRIDGE REFERENCE ELECTRODE

[75] Inventors: Leon P. Sudrabin, Berkeley Heights; Stephen F. Billets, Cedar Grove; Van Dyke J. Pollitt, Fanwood; Lubomyr Liszczynsky, Cedar Grove, all of N.J.

[73] Assignee: Pennwalt Corporation, Philadelphia, Pa.

[21] Appl. No.: 919,600

[22] Filed: Jun. 27, 1978

Related U.S. Application Data

[63] Continuation of Ser. No. 769,380, Feb. 17, 1977, abandoned.

[51] Int. Cl.³ .............................. G01N 27/30
[52] U.S. Cl. ................................... 204/195 F
[58] Field of Search ...................... 204/195 F

[56] References Cited

U.S. PATENT DOCUMENTS

| | | | |
|---|---|---|---|
| 2,338,713 | 1/1944 | Ewing | 204/195 F |
| 3,000,804 | 9/1961 | Cahoon et al. | 204/195 F |
| 3,192,144 | 6/1965 | Heuze | 204/195 F |
| 3,471,394 | 10/1969 | Sudrabin | 204/195 F |
| 3,493,484 | 2/1970 | Berg et al. | 204/195 R |
| 3,926,764 | 12/1975 | Ruzicka et al. | 204/195 F |
| 4,002,547 | 1/1977 | Neti et al. | 204/195 F |

FOREIGN PATENT DOCUMENTS

2605149  9/1976  Fed. Rep. of Germany ....... 204/195 F

OTHER PUBLICATIONS

Scott, "The Copper Sulfate Electrode", presented at meeting of National Association of Corrosion Engineers, South Central Region, San Antonio, Texas on Oct. 23, 1956, 5 pages.

Primary Examiner—G. L. Kaplan
Attorney, Agent, or Firm—Charles N. Quinn

[57] ABSTRACT

A salt bridge reference electrode, immersible in an electrolyte, contains a metal electrode contacting water saturated salt crystals and is configured so both evaporative loss of contained water and diffusion loss of contained salt crystals are minimal. An electrolytically conductive plug, having metallic salt crystals in suspension, within the cell, maintains electrolytic continuity between the water-saturated salt crystals and the surrounding electrolyte while minimizing loss of salt crystals from the saturated water into the surrounding electrolyte by osmosis.

9 Claims, 2 Drawing Figures

SALT BRIDGE REFERENCE ELECTRODE

This is a continuation of application Ser. No. 769,380, filed Feb. 17, 1977 and now abandoned.

BACKGROUND OF THE INVENTION

This invention relates to salt bridge reference electrodes used in cathodic protection systems which protect metal structures immersed in corroding electrolytes. Such reference electrodes produce a fixed voltage potential, to which voltage potential of the metal structure being protected is compared, to regulate operation of a cathodic protection system which provides protective current to the metal structure of interest. Such reference electrodes must remain stable, i.e. fixed in voltage potential, for extended periods of time.

DESCRIPTION OF THE PRIOR ART

A salt bridge reference electrode is described in U.S. Pat. No. 3,471,394 and is a vertically oriented reference electrode containing a bath of water saturated with metallic salt crystals with the water solution in contact with a metallic electrode which is electrochemically related to the salt. The reference electrode disclosed in U.S. Pat. No. 3,471,394 operates successfully so long as the reference electrode is maintained vertical. However when the reference electrode of U.S. Pat. No. 3,471,394 is displaced from a vertical orientation, loss of salt from the water-salt solution is greatly accelerated thereby substantially shortening the useful life of the reference electrode. Furthermore the reference electrode disclosed in U.S. Pat. No. 3,471,394 cannot be buried directly in a corroding electrolyte, such as soil, unless a reservoir of liquid electrolyte, such as water, is supplied to maintain moisture for the saturated salt crystals. Many cathodic protection system applications require reference electrodes which can be oriented at substantial angles from the vertical and/or which can be buried in soil or some other corroding electrolyte without an associated resevoir of liquid electrolyte, such as water, being buried therewith.

A reference electrode which need not be maintained in a vertical orientation and which may be buried in soil or immersed in another corroding electrolyte is disclosed in a paper "The Copper Sulfate Electrode" presented by Gordon N. Scott at a meeting of the National Association of Corrosion Engineers, South Central Region, at San Antonio, Texas on Oct. 23, 1956. This type of reference electrode continues to be commercially popular as evidenced by Harco Corporation's product bulletin "Permanent Water-Storage Tank Reference Electrode". Both Harco Corporation and Far West Engineering Company currently employ the Scott reference electrode. The Scott approach is to provide a reference electrode consisting of a copper electrode embedded in a cylinder of copper sulfate crystals mixed with plaster of paris. The Scott reference electrode polarizes, i.e. changes its produced reference voltage, readily, This leads to unreliable measurements of the cathodically protected structure's voltage potential. It has been found that a current flow of 5.0 microamperes polarizes the Scott reference electrode by 0.071 volts after 5 minutes and by 0.096 volts after 2 hours. The high polarization of the Scott electrode is attributable to restricted migration of copper ions through the plaster of paris to the electrode-corroding electrolyte interface when copper ions are reduced at the copper rod. This depletion of copper ions at the electrode surface alters the reference electrode potential. As a further disadvantage, the Scott electrode, when dry, has a resistance to the environment of several million ohms. This high resistance limits use of the Scott electrode to extremely high impedance voltmeters.

SUMMARY OF THE INVENTION

The present invention provides a fixed potential salt bridge reference electrode which can be buried at any orientation in a corroding electrolyte and which produces a fixed voltage potential for an extended period of time while buried. The salt bridge reference electrode exhibits minimal polarization and is suitable for use with a wide variety of cathodic protection systems.

DESCRIPTION OF THE PREFERRED EMBODIMENTS

Figure 1:
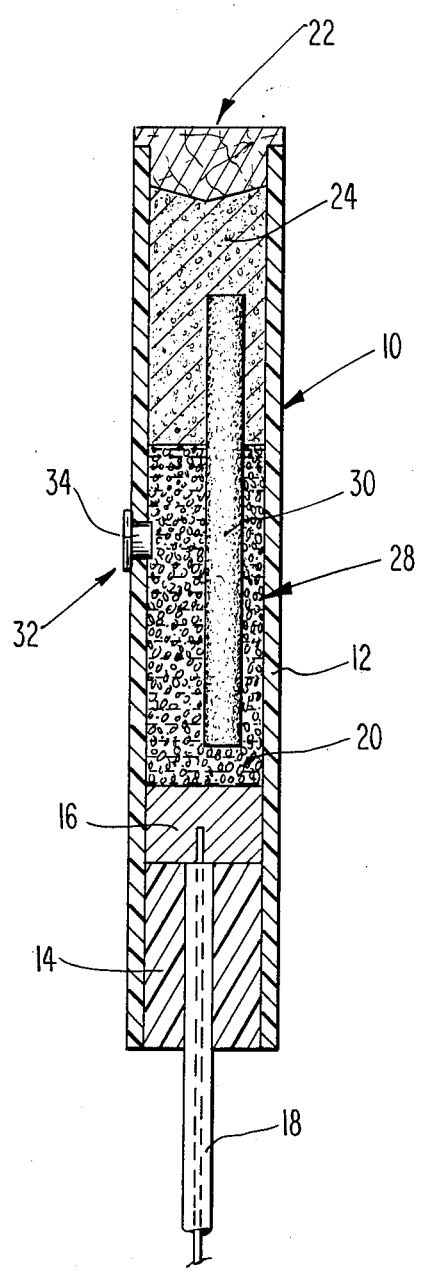
FIG. 1 is a sectional view of a preferred embodiment of a salt bridge reference electrode embodying the invention.

Referring to FIG. 1, the fixed potential salt bridge reference electrode includes an electrolytically non-conductive generally axially elongated vessel, designated generally 10, which has an open end designated generally 22, and which is comprised of a cylindrical tube 12, forming the wall of vessel 10, and an epoxy plug 14 which forms the closed end of the vessel. A metallic electrode 16 is contained within the vessel, and is preferably embedded in and extending from plug 14 at an end opposite vessel open end 22. An electrically insulated lead wire 18 provides means for electrically connecting electrode 16 to a voltage potential measuring device, not shown. Wire 18 passes through epoxy plug 14. Within tube 12 at an end remote epoxy plug 14 is porous plug 24 which has crystals of a chosen salt (of the metal from which electrode 16 is formed) suspended therein such that the metallic salt crystals are dispersed throughout the plug. The space between plug 24 and epoxy plug 14, surrounded by tube 12, defines a compartment 28 which has resident therein water 20 saturated with crystals of the chosen salt of the electrode metal. Surplus crystals are provided to ensure that water 20 remains saturated. A port 32 through tube 12 allows water to be filled into compartment 28. A removable cap 34 closes port 32. At open end 22 of tube 12 is a semi-permeable membrane, preferably formed of wood with the wood grain parallel to the longitudinal axis of the tube, which inhibits escape of salt ions from the vessel. Extending into compartment 28 is a rod-like extended portion 30 of porous plug 24. Rod-like portion 30 insures electrochemical connection of the saturated solution 20 with plug 24 even if the amount of water in compartment 28 is substantially less than the total volume of the compartment and even if the reference electrode is oriented nonvertically.

The metal of electrode 16 and the metallic salt of solution 20 are mutually selected to provide a reference cell of fixed potential and may be any of the combinations of electrode metals and salts conventionally used in salt bridge cells. Preferably the metal of electrode 16 is copper while water 20 is an aqueous solution of copper sulfate, with an excess supply of copper sulfate crystals within compartment 28 to maintain the saturated characteristic of the solution. Optionally, electrode 16 may be cadmium and the chosen metallic salt cadmium sulfate. The metallic electrode may also be a mixture of mercury and mercurous chloride with the chosen metallic salt potassium chloride. A further possibility is that electrode 16 may be silver and silver chloride with the chosen metallic salt potassium chloride.

Porous plug 24 is formed of crystals of the chosen metallic salt mixed with any material which is porous; thus plug 24 is electrolytically conductive when moist. Plaster of paris, concrete or porous resins may be used. Plug 24 is preferably poured in place and is preferably between about 20 percent to about 30 percent metallic salt crystals. When plug 24 is a plaster of paris-metallic salt crystal mixture and it is desired to increase the porosity of the plug, up to 30 percent bentonite may be added to the plaster of paris before the plug is poured in place.

When the reference electrode is buried in a dry soil electrolyte, it is desirable that a humectant, such as Sorbital, ethylene glycol or propylene glycol be added in 1:1 proportion to water 20 to insure that sufficient moisture is retained in the reference cell to maintain a stable potential. (Sorbital is a registered trademark of ICI America, Inc., Wilmington, Delaware).

After the supply of metallic salt crystals has been placed in compartment 28, if compartment 28 is filled with water, when cap 34 is pressed into port 32 some of water 20 will be displaced into plug 24 thereby maintaining electrolytic conductance between electrode 16 and the surrounding corroding electrolyte in which the reference cell is buried.

When porous plug 24 is made of crystals of the chosen metallic salt admixed with plaster of paris, it has been found to be advantageous to add a 50:50 solution of water and humectant directly to the plaster of paris-salt crystal mix before pouring plug 24 in place. This results in further assurance of maintenance of electrolytic conductance between electrode 16 and the surrounding corroding electrolyte. Moreover, if compartment 28 is filled with a water-Sorbital solution after the metallic salt crystals are placed in the compartment, as cap 34 is pressed into port 32 some of the water-Sorbital solution will be forced into plug 24, providing even greater assurance of maintenance of moisture in plug 24 and resultant electrolytic conductance between electrode 16 and the surrounding corroding electrolyte.

Additionally, when porous plug 24 is made of crystals of the chosen metallic salt admixed with plaster of paris and the reference electrode is to be immersed in a corroding saline electrolyte, it is desirable to admix about one percent silver nitrate with the portion of plug 24 which is proximate open end 22. This prevents migration of chloride ions from the saline electrolyte to the surface of electrode 16.

Figure 2:
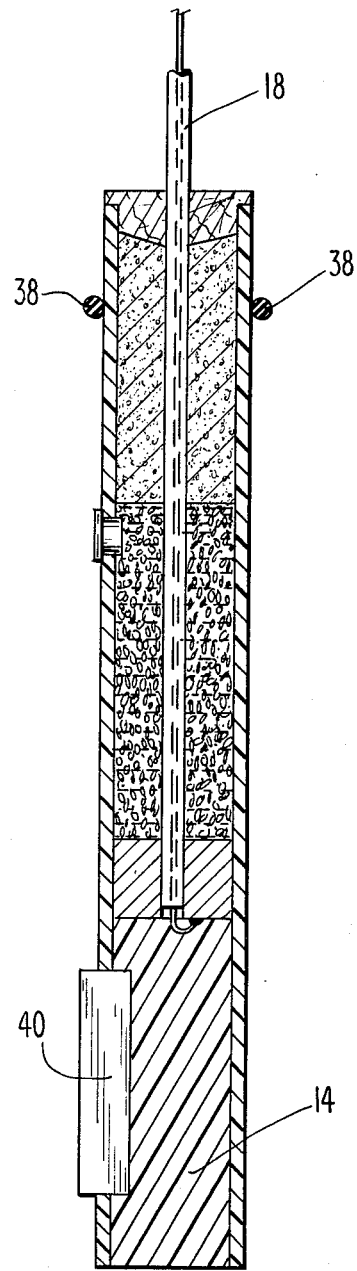
FIG. 2 is a sectional view of a second embodiment of a salt bridge reference electrode embodying the invention.

FIG. 2 illustrates an embodiment of the reference electrode adapted for use with the ice-free self-releasing water tank anode suspension system disclosed and claimed in U.S. Pat. No. 3,954,591. The reference electrode illustrated in FIG. 2 is similar to that shown in FIG. 1. Additionally the reference electrode illustrated in FIG. 2 includes a permanent magnet 40 secured to tube 12 and having a portion thereof embedded within epoxy plug 14. The magnet provides means for maintaining the reference electrode immediately adjacent the wall of a steel water tank. This allows potential of the steel to be compared to fixed potential of a proximate, firmly attached electrode. A thin, electrically insulative coating applied to magnet 40 prevents metal-to-metal contact thereby avoiding any magnet-water tank wall interaction which could affect potential within the reference cell. "O" ring 38 spaces the reference electrode slightly away from the steel water tank structure. Such spacing prevents metallic bridging by cathodic reduction of copper ions which might otherwise diffuse from the electrode to the steel tank structure.

It has been found that the reference electrode disclosed herein polarizes less than 0.01 volts with a test current of 80 microamperes, and polarizes only about 0.035 volts with a test current of 800 microamperes.

Having thus described our invention we claim the following:

1. A position-insensitive long-term fixed potential internally wet salt bridge reference electrode assembly immersible in wet and dry corroding electrolytes, comprising:
    (a) an electrolytically non-conductive generally axially elongated vessel impervious to water, having an open end;
    (b) a metallic electrode contained within said vessel, remote from said vessel open end;
    (c) insulated wire means, physically connected to said metallic electrode and extending from the exterior of said vessel, for electrically connecting said metallic electrode to a voltage potential measuring device;
    (d) a hydrophylic porous electrolytically conductive plug circumscribed by an inner surface of a generally cylindrical wall of said vessel, including electrolytically active metallic salt crystals suspended therein with the salt crystals dispersed throughout the plug, said plug separating said metallic electrode from said vessel open end, an extremity of said plug most proximate said metallic electrode being spaced from said metallic electrode to form a closed compartment bounded by said plug, said metallic electrode and the wall of said vessel, said plug including:
        (i) a rod-like portion extending into said compartment towards said metallic electrode, for contacting salt crystal-saturated water in said compartment and maintaining simultaneous water-plug and water-electrode contact even when water volume is substantially less than compartment volume and said electrode is oriented with said axially elongated tube substantially skew to vertical;
    (e) said water, being saturated with crystals of said metallic salt, and being within said compartment for unrestricted flow therethroughout;
    (f) hydrophylic electrolytically semipermeable barrier means, disposed across said vessel open end, one surface thereof contacting said plug and a second surface thereof forming an external surface of said assembly to contact said electrolyte when said assembly is immersed therein, for resisting escape of ions of said salt for said vessel;
wherein said water contacts both said electrode and said plug.

2. The assembly of claim 1 wherein a humectant is added to said water.

3. The assembly of claim 2 wherein said humectant is chosen from the group consisting of Sorbitol, ethylene glycol and propylene glycol.

4. The assembly of claim 1 wherein said metallic electrode is copper and said salt is copper sulphate.

5. The assembly of claim 1 wherein said metallic electrode is cadmium and said salt is cadmium sulphate.

6. The assembly of claim 1 wherein the porous material of said plug is plaster of paris.

7. The assembly of claim 6 wherein said plug has silver nitrate admixed with the plaster of paris and salt crystals, at the portion of the plug proximate said vessel open end.

8. The assembly of claim 1 wherein the porous material of said plug is concrete.

9. The assembly of claim 1 wherein the porous material of said plug is a resin.

* * * * *